United States Patent [19]
Roos et al.

[11] Patent Number: 5,554,381
[45] Date of Patent: * Sep. 10, 1996

[54] LOW FLUX MATRIX SYSTEM FOR DELIVERING POTENT DRUGS TRANSDERMALLY

[75] Inventors: Eric J. Roos, Marlborough, Mass.; Chia-Ming Chiang, Foster City, Calif.; Tsung-Min Hsu, Taipei, Taiwan

[73] Assignee: Cygnus, Inc., Redwood City, Calif.

[ * ] Notice: The portion of the term of this patent subsequent to Oct. 12, 2010, has been disclaimed.

[21] Appl. No.: 104,414

[22] Filed: Aug. 9, 1993

[51] Int. Cl.$^6$ ............................................. A61L 15/24
[52] U.S. Cl. ...................... 424/449; 424/448; 424/487; 602/54
[58] Field of Search ................... 424/486, 487, 424/448, 449; 602/52, 54

[56] References Cited

U.S. PATENT DOCUMENTS

| | | | |
|---|---|---|---|
| 4,906,169 | 3/1990 | Chien et al. | 424/448 |
| 4,994,267 | 2/1991 | Sablotski | 424/484 |
| 5,145,682 | 9/1992 | Chien et al. | 424/448 |
| 5,252,334 | 10/1993 | Chiang et al. | 424/448 |
| 5,300,291 | 4/1994 | Sablotsky et al. | 424/448 |
| 5,393,529 | 2/1995 | Hoffmann et al. | 424/445 |

FOREIGN PATENT DOCUMENTS

WO91/03219  3/1991  WIPO.

*Primary Examiner*—Edward J. Webman
*Attorney, Agent, or Firm*—Morrison and Foerster

[57] ABSTRACT

Matrix-type transdermal drug delivery devices for administering potent steroids such as ethinyl estradiol at a low flux steady-state rate over a multi-day period comprising a laminate of: (a) an occlusive backing layer and (b) a matrix layer of the drug completely dissolved at a loading of below 0.5% by weight in a 2-ethylhexyl acrylate copolymer.

7 Claims, 4 Drawing Sheets

LOW FLUX MATRIX SYSTEM FOR DELIVERING POTENT DRUGS TRANSDERMALLY

DESCRIPTION

1. Technical Field

This invention is in the field of transdermal drug delivery. More specifically it relates to matrix-type transdermal drug-delivery devices which deliver potent drugs in a low flux steady-state regimen over a multi-day period.

2. Background

PCT/US90/04767 (Pub. No. WO 91/03219) describes a solid matrix system for administering steroid drugs, including potent estrogens and progestogens such as gestodine and ethinyl estradiol transdermally. That system is composed of a backing layer and a matrix layer of an acrylate copolymer and the system is capable of delivering the steroids at practical flux levels without using a permeation enhancer. The application states that the matrix typically contains 0.5% to 25% by weight drug. It does not describe the kinetics of the release of drug from the matrix.

The present invention is directed to novel embodiments of the system described in PCT/US90/04767 in which the drug is a highly potent drug that is highly soluble in the acrylate copolymer and the loading of drug in the matrix is below 0.5% by weight. Such embodiments provide a low flux steady-state delivery pattern over a multi-day period.

DISCLOSURE OF THE INVENTION

This invention is a transdermal drug-delivery device for administering therapeutically effective amounts of a potent drug at a steady-state delivery rate over a multi-day period comprising a laminate of:

(a) a backing layer that is substantially impermeable to the drug;

(b) a basal matrix layer of a mixture of the drug and an adhesive copolymer of 2-ethylhexyl acrylate and at least one comonomer selected from the group consisting of vinyl acetate, acrylic acid, and methyl acrylate, wherein the drug is completely dissolved in the matrix and the loading of drug in the matrix is below 0.5% by weight.

MODES FOR CARRYING OUT THE INVENTION

Figure 1:
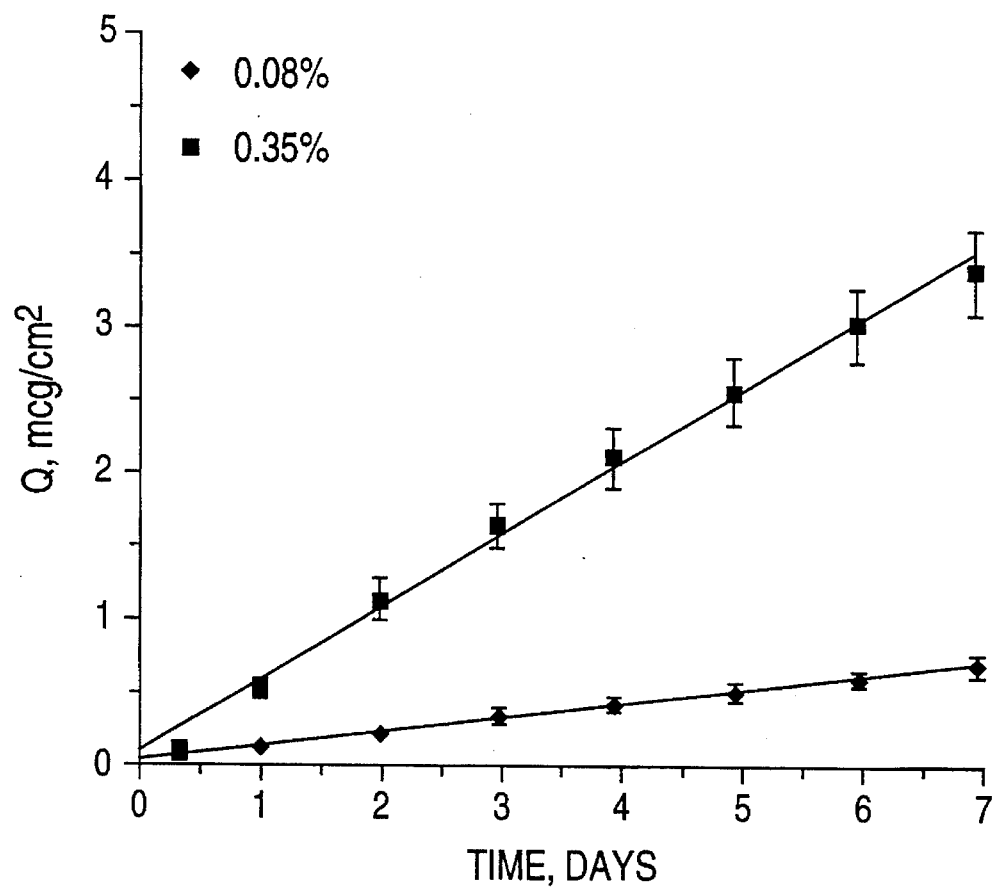
FIGS. 1–4 are graphs of the skin flux test data obtained from the composites described in the examples, infra.

As used herein, "matrix-type" denotes a device in which the drug reservoir is a solid matrix of a homogeneous mixture of drug and a pressure-sensitive adhesive. Typically one surface of the matrix will define the basal surface (i.e., that surface which contacts the skin and forms a diffusional pathway for the drug to migrate from the device to the skin) of the device.

The term "transdermal" is intended to denote transport through skin or mucosa such as the buccal mucosa.

The term "therapeutically effective amount" denotes that dose of drug that will provide the pharmacological effect for which the drug is indicated.

The term "potent" intends drugs that are therapeutically effective at doses below about 1 mg/day, more typically below about 0.2 mg/day. Examples of such drugs are ethinyl estradiol, gestodine, mestranol, 3-keto-desogestrol, levonorgestrol, and norgestimate. These drugs may be administered singly or in combination depending upon the condition being treated. For instance, combinations of estrogens or combinations of estrogens and progestogens may be administered to provide hormone replacement therapy.

The term "steady state" intends a substantially constant skin flux over the multi-day administration period (after the initial 6–8 hr of wearing). Expressed quantitatively "steady state" intends that the correlation coefficient of the plot of the cumulative amount of drug released (measured in vitro) versus time (after the initial 2–8 hr) is $\geq 0.9$.

The term "skin flux" intends the rate of drug transmitted through skin per unit time as determined by the procedure described in PCT/US90/04767. For ethinyl estradiol the desired flux will normally be 0.1 to 0.5 $\mu g/cm^2/day$.

The term "multi-day" period denotes a period of at least two days, typically two to fourteen days.

The term "highly soluble" denotes a solubility of the drug in the matrix that is at least 2% w/v (20 mg/ml), more usually at least 5% w/v (50 mg/ml).

The adhesive copolymer of the matrix is a copolymer of 2-ethylhexyl acrylate and vinyl acetate, acrylic acid and/or methyl acrylate. The weight ratio of 2-ethylhexyl acrylate to the comonomer(s) is typically in the range of 90:10 to 60:40. These copolymers may be used separately or in mixtures. These copolymers are solvent-based and form films upon casting and solvent removal. The resulting films are solid; i.e., they are tacky, amorphous and essentially non-flowing. Embodiments of these copolymers are commercially available in solution under the brand names GELVA (available from Monsanto Chemical Company) and MORSTIK (available from Morton Thiokol, Inc.). The solvents are organic solvents such as toluene, alkanols (ethanol, isopropanol), ethyl acetate, and the like. Specific commercial examples of these copolymers are GELVA 737 (approximately 72 wt. % 2-ethylhexyl acrylate, 28 wt. % vinyl acetate), GELVA 788 (approximately 70 wt % 2-ethylhexyl acrylate, 30 wt % vinylacetate), and MORSTIK 607 (approximately 85 wt. % 2-ethylhexyl acrylate, 10 wt. % methyl acrylate, 3 wt. % acrylic acid, 2 wt % vinyl acetate) and DUROTAK 280-2516 (approximately 67 wt % 2-ethylhexylacrylate, 28 wt % vinylacetate, 5% hydroxyl-containing monomer).

Known skin permeation enhancers may be included in the matrix provided the drug remains solubilized in the matrix. Enhancers may be used to achieve higher levels of skin flux or to offset a decrease in skin flux attributable to a substantial decrease in the concentration of drug in the matrix over time. Specific examples of permeation enhancers that may be used are those described in U.S. Pat. Nos. 4,906,463 and 5,006,342.

In embodiments of the invention that are intended for extended wear (e.g., about 5 or more days) it is desirable to include minor amounts (i.e., 2% to 15% by weight, usually 5% to 10% by weight) of a hydrophilic viscosity reducing agent in the matrix. Examples, without limitation, of such agents are silica gel, calcium silicate, gelatin, methylcellulose, hydroxyethylcellulose, hydroxypropylmethylcellulose, polyvinylpyrollidine, and polyvinylalcohols.

The thickness of the matrix layer will usually be in the range of 25 to 100 microns.

The devices of this invention exhibit a linear correlation between drug loading and skin flux. This is due to the high drug solubility in the matrix and the low loading of drug in the matrix. As indicated the drug loading is < 0.5% by weight. Drug loading will normally be between 0.05% and 0.35% by weight. (The low loading of drug may be correlated to the amount of drug needed for therapy in order to have minimal amounts of residual drug left in the matrix at the end of the multi-day wearing period.)

The backing layer of the device is substantially impermeable to the drug and preferably occlusive (an occlusive layer exhibits a water vapor transmission rate below about 26 g/m$^2$/day. In addition to preventing drug escaping from the top surface of the device and maintain the desired degree of occlusivity, the backing layer provides structural support for the device. The thickness of the backing will usually be in the range of 0.5 to 5 mils. The backing materials described in PCT/US90/04767, the disclosure of which is incorporated herein by reference, may be used in the devices of this invention.

The area of the basal surface of the device through which drug is transmitted by diffusion to the skin will typically be in the range of 2.5 to 20 cm$^2$. The particular area will be correlated with the skin flux to provide the requisite daily drug dose to provide therapy. For ethinyl estradiol the daily dose will be in the range of about 0.25 to 10 µg/day. In the case of ethinyl estradiol the flux will typically be 0.004 to 0.025 µg/cm$^2$/hr.

The devices may be fabricated by the procedures described in PCT/US90/04767.

The following examples further illustrate this invention. These examples are not intended to limit the invention in any manner.

EXAMPLES

Example 1

Ethinyl estradiol (EE), Morstik 607, and silica gel (0.08:89.92:10) were blended together in a 250 ml container for 1 hr at room temperature. The blend was cast onto a 50 micron thick Melinex 442/200 polyester backing and dried in an oven at 70° C. The resulting laminated composite was designed to exhibit an in vitro skin flux of 0.10 µg/cm$^2$/day over 7 days.

A second composite was similarly constructed using an EE:Morstik 607:silica gel ratio of 0.35:89.65:10. This composite was designed to provide an in vitro flux of 0.5 µg/cm$^2$/day over 7 days.

Skin flux tests were carried out on these composites as described in PCT/US90/04767. The results of these tests are summarized in FIG. 1 and in the following table. In FIG. 1, a linear regression analysis of the 0.08% data points produced a line of the equation y=2.9888e−2+9.6043e−2x. The residual value (R$^2$) is 0.993. The equation of the line corresponding to the 0.35% data points is y=7.7341e-2+0/49175x with a R$^2$ value of 0.0995. As shown in the Figure and Table, skin flux from the composite was substantially constant.

TABLE

| Formulation | Target Skin Flux (µg/cm$^2$/day) | Mean Skin Flux (µg/cm$^2$/day) |
|---|---|---|
| 0.08% EE | 0.10 | 0.11 ± 0.05 (n = 24) |
| 0.35% EE | 0.50 | 0.55 ± 0.16 (n = 20) |

Example 2

Figure 2:
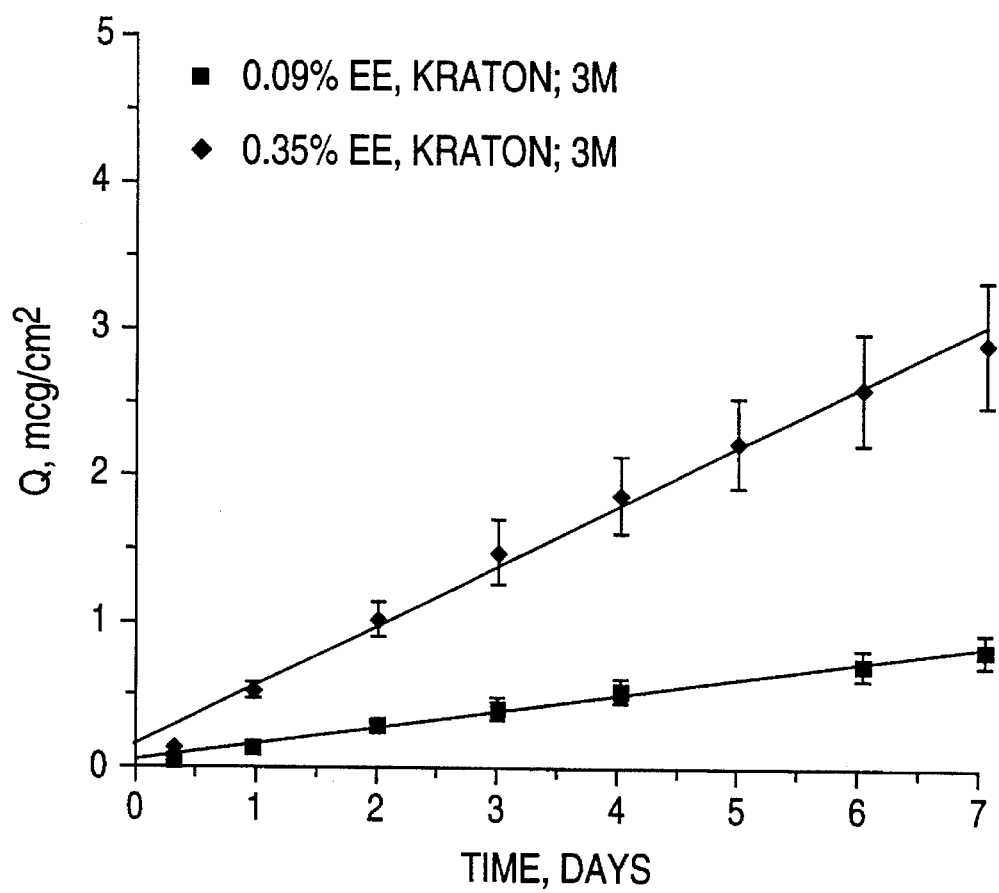
Figure 3:
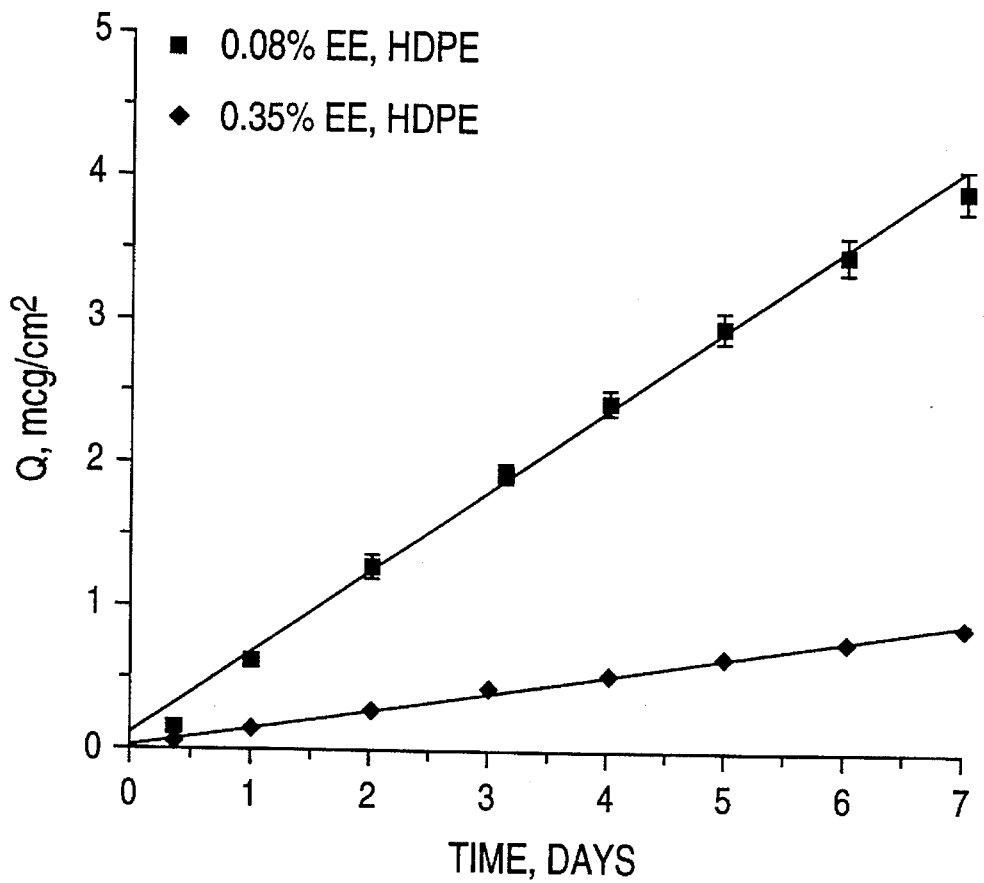
Figure 4:
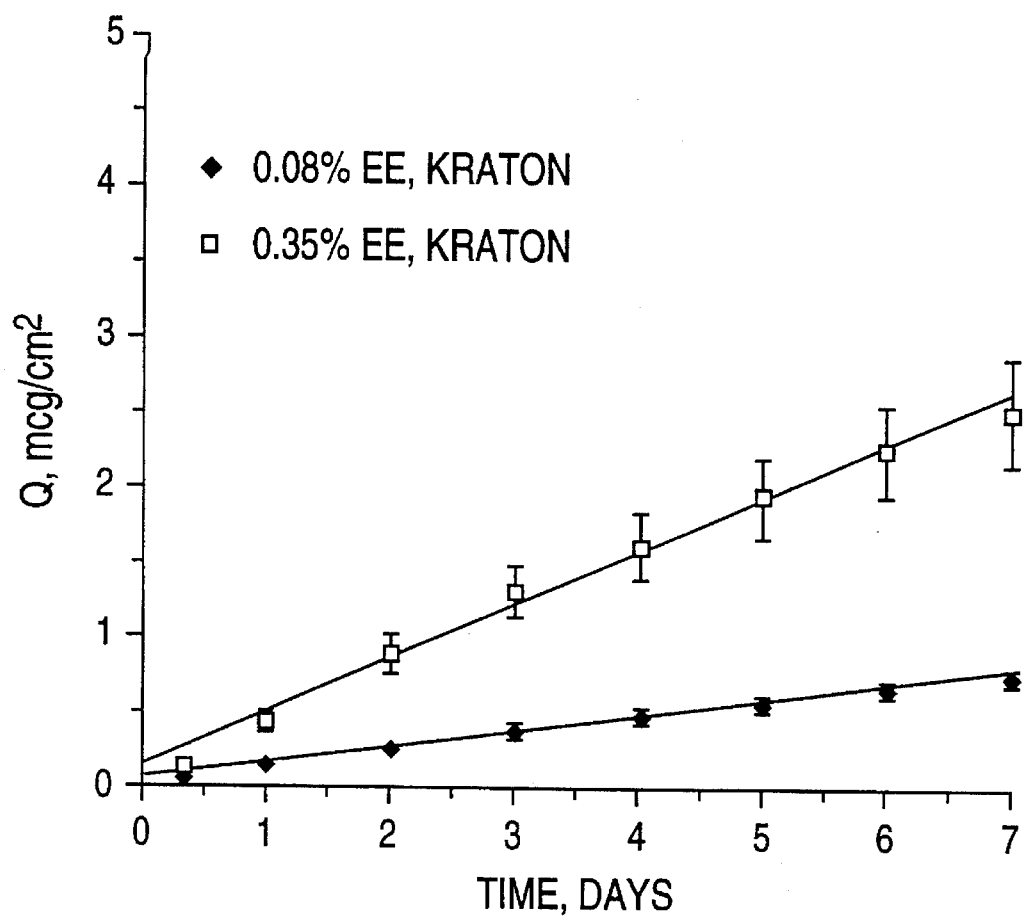

Composites were made as in Example 1 using three different backing materials: Killion Kraton, 5 mils; high density polyethylene, 2.5 mils, and Noslo Kraton, 5 mils. FIGS. 2–4 are graphs of the skin flux test data obtained from those composites. In FIG. 2, linear regression analysis of the 0.09% data points indicated the equation of this line is y=4.7809e-2+0.11393x with an R$^2$ value of 0.991. The equation of the 0.35% line is y=0.14565+0.40928x with an R$^2$ value of 0.992. In FIG. 3, the 0.08% line is y=2.7291e-2+0.12219x with an R$^2$ value of 0.993. The 0.35% line is y=8.9679e-2+0.56275x with an R$^2$ value of 0.995. In FIG. 4, the equation of the line produced by the 0.08% data points is y=4.1235e-2+0.10096x with an R$^2$ value of 0.992 and the 0.35% line is y=0.11560+0.35564x with an R$^2$ value of 0.992. As shown each performed essentially equivalent to its counterpart of Example 1.

Modifications of the above described modes for carrying out the invention that are obvious to those of skill in the fields of pharmaceuticals, transdermal drug delivery, and related fields are intended to be within the scope of the following claims.

We claim:

1. A transdermal drug delivery device for administering therapeutically effective amounts of a potent drug at a steady-state delivery rate over a multi-day period comprising a laminate of:
   (a) a backing layer that is occlusive to the drug; and
   (b) a basal matrix layer of an adhesive copolymer comprising 2-ethylhexyl acrylate and a comonomer selected from the group consisting of vinyl acetate, acrylic acid, methyl acrylate, and mixtures thereof, wherein the drug is completely dissolved in the matrix and the loading of the drug in the matrix is below 0.5% by weight.

2. The device of claim 1 wherein the drug is ethinyl estradiol, said rate is 0.25 to 10 µg/day, and the loading is in the range of 0.08 to 0.35% by weight.

3. The device of claim 1 wherein the basal matrix layer includes 2% to 15% by weight of a hydrophilic particulate viscosity reducing agent.

4. The device of claim 3 wherein the agent is silica gel.

5. The device of claim 1 wherein the solubility of the drug in the matrix is at least 2% w/v.

6. The device of claim 2 wherein the basal matrix layer includes 5% to 10% by weight silica gel and the copolymer is a copolymer of 2-ethylhexylacrylate, methylacrylate, acrylic acid, and vinylacetate.

7. The device of claim 1 wherein the drug is ethinyl estradiol, gestodine, mestranol, 3-ketodesogestrol, levonorgestrol, norgestimate, or mixtures thereof.

* * * * *